United States Patent [19]

Roper

[11] Patent Number: 4,541,287
[45] Date of Patent: Sep. 17, 1985

[54] METHOD OF MEASURING METAL COATING ADHESION

[75] Inventor: John R. Roper, Northglenn, Colo.

[73] Assignee: The United States of America as represented by the United States Department of Energy, Washington, D.C.

[21] Appl. No.: 479,761

[22] Filed: Mar. 28, 1983

[51] Int. Cl.[4] ............................................. G01N 3/08
[52] U.S. Cl. ....................................... 73/827; 73/856
[58] Field of Search ................... 73/827, 856, 842, 834

[56] References Cited

U.S. PATENT DOCUMENTS 3,580,065  5/1971  Strittmater ............................. 73/827
3,605,486  9/1971  Anderholm et al. .................. 73/827

FOREIGN PATENT DOCUMENTS 0029792  3/1977  Japan ..................................... 73/827

Primary Examiner—Anthony V. Ciarlante
Attorney, Agent, or Firm—James H. Chafin; Albert Sopp; Judson R. Hightower

[57] ABSTRACT

A method for measuring metal coating adhesion to a substrate material comprising the steps of preparing a test coupon of substrate material having the metal coating applied to one surface thereof, applying a second metal coating of gold or silver to opposite surfaces of the test coupon by hot hollow cathode process, applying a coating to one end of each of two pulling rod members, joining the coated ends of the pulling rod members to said opposite coated surfaces of the test coupon by a solid state bonding technique and finally applying instrumented static tensile loading to the pulling rod members until fracture of the metal coating adhesion to the substrate material occurs.

8 Claims, 6 Drawing Figures

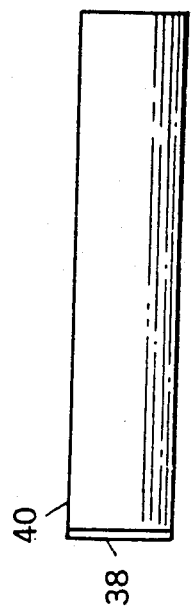
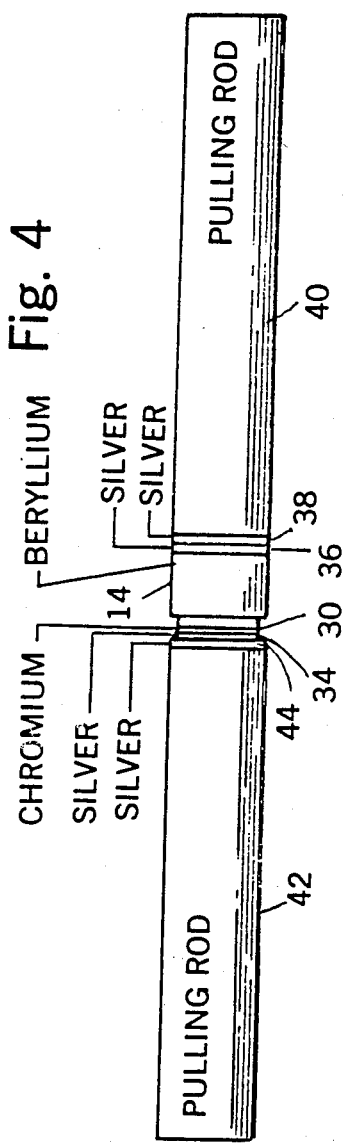
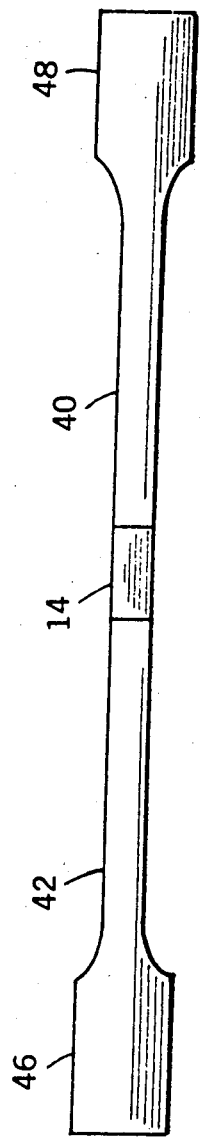

METHOD OF MEASURING METAL COATING ADHESION

The United States Government has rights in this invention pursuant to Contract No. DE-AC04-76DPO3533 between the Department of Energy and Rockwell International.

BACKGROUND OF THE INVENTION

1. Field of the Invention

The present invention relates to a method of measuring adhesion strength and more particularly, but not by way of limitation, to a method of measuring the adhesion strength of a metal coating applied to a second metal substrate material.

2. History of the Prior Art

Metal coatings of nickel, chromium, aluminum and other materials have been applied to various substrates in a multitude of industrial applications.

However, the testing of the quality of adhesion to the metal coating has been lacking. Although many qualitative tests, such as scratch tests and peel tests are in use, these tests do not provide precise quantitative measurements of the adhesive strength of the metal coating to the substrate material.

Research and development of good coating techniques and a study of the factors influencing adhesion would be greatly enhanced by method for quantitative measurement of the adhesive strength of the coating.

SUMMARY OF THE INVENTION

The present invention provides a method of obtaining accurate quantitative measurements of the adhesive strength of metal coatings which have been applied to substrate materials. The method takes advantage of the excellent film adherence characteristics of a hot hollow cathode (HHC) coating process and the relatively low temperature joining capabilities of a gold or silver solid state bonding (SSB) process.

The method generally consists of preparing a test specimen or coupon of substrate material having the coating of interest applied to one surface of the coupon. For ease of handling, the coupon may be in the form of a cylinder or disk with one end surface coated with the metal material and using the process to be tested.

Both ends or surfaces of the coupon are then coated with silver or gold using a hot hollow cathode process. The gold or silver is thus very firmly bound to the metal coating on one end of the specimen and to the substrate material at the opposite end of the specimen.

The HHC deposited gold or silver film process can provide an adhesion strength as high as one hundred kips per square inch (ksi) depending on the strength of the bulk material being coated while the SSB joining process requires joining pressures of from 10 to 20 ksi. Therefore, if the substrate to be tested can survive bonding loads of at least 10 ksi without extensive plastic deformation and the adhesion strength of the coating of interest is less than one hundred ksi, the present method can be used to accurately measure the adhesive strength of the coating to the substrate material.

The HHC process is then used to coat one end of each of two pulling rods which should of course have compressive and tensile strength at least as great as that of the substrate material and the metal coating bond in question.

The pulling rods are then attached to opposite surfaces of the specimen by the solid state bonding process for attaching gold-to-gold or silver-to-silver. This is accomplished by applying a compressive load to each end of the pulling rods at a predetermined temperature for a given amount of time. After the test unit has been joined with the specimen sandwiched between the pulling rods, the unit may be machine-turned to form a waist portion of a uniform diameter in a region containing the specimen.

The unit may then be mounted in a conventional instrumented tensile loading machine for static tensile loading, thereby pulling the pulling rods until failure of the metal coating adhesion to the substrate material occurs. Static loading is defined as applying the load slowly enough that all parts of the specimen are essentially in equilibrium at any given instant.

Naturally, if during the loading, creep (plastic elongation) of the specimen occurs, quantitative measurement of the adhesion will not be obtained but it would establish that the adhesion strength of the coating is at least as great as the tensile strength of the substrate material.

DESCRIPTION OF THE DRAWINGS

Other and further advantageous features of the present method will hereinafter more fully appear in connection with a detailed description of the drawings in which:

FIG. 4 is a sectional view of a pulling rod having an HHC coating at one end thereof.

FIG. 5 is an elevational view of an assembled test unit.

FIG. 6 is an elevational view of the test unit of FIG. 5 after being machined into a test configuration.

DESCRIPTION OF THE PREFERRED METHOD

Figure 2:
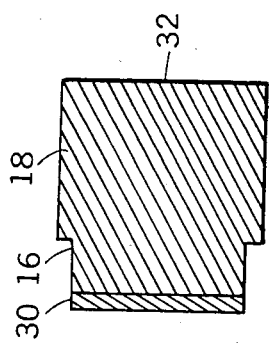
FIG. 2 is a sectional view of one of the coupons having a metal coating applied thereto.
Figure 3:
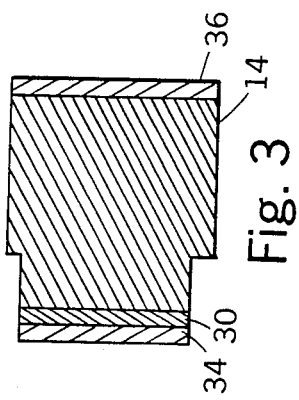
FIG. 3 is a sectional view the coupon of FIG. 2 having an HHC coating applied to each end thereof.

The following is a detailed description of the method which is the subject of the present invention in a particular application.

The objective of the application was to measure the coating adhesion strength of a physical vapor deposition (PVD) chromium coating applied to the interior surface 10 of a hemispherical beryllium substrate generally indicated by reference character 12.

Figure 1:
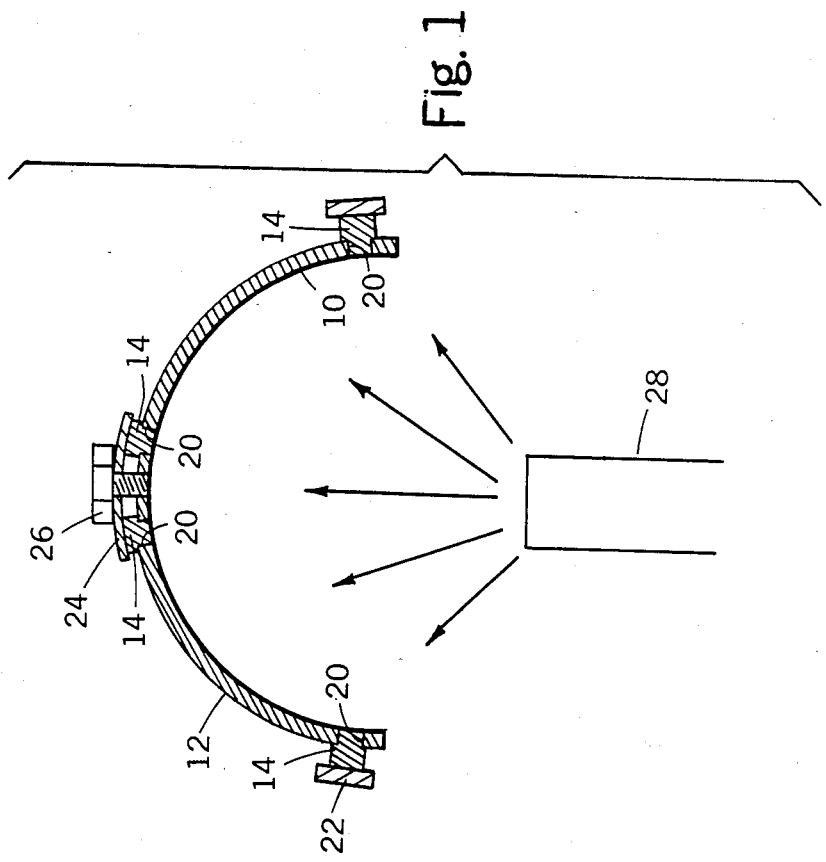
FIG. 1 is a sectional view of an example of test coupon preparation.

A plurality of beryllium specimens indicated by reference character 14 consisted of beryllium cylinders having a cylindrical portion 16 and enlarged portion 18. The cylindrical portion 16 is inserted into holes 20 in the hemispherical wall at locations of interest as shown in FIG. 1. The specimens or coupons 14 were firmly secured to the beryllium substrate by means of a band 22 and by a plate and bolt assembly indicated by reference characters 24 and 26. During the deposition process, the hemispherical shell is heated to approximately 450 degrees centigrade and preliminary work showed that it was necessary to securely clamp the beryllium coupons into place in order to ensure good thermal equilibrium between the coupons and the hemispherical shell.

The inside of the entire assembly was then cleaned by grit blasting and was coated by physical vapor deposition (PVD) chromium film from a chromium source indicated by reference character 28. This resulted in a uniform layer of chromium indicated by reference character 30 in FIG. 2 of the drawings being applied to one end of each coupon 14 in question.

Both the coated end surface 30 and the opposite surface 32 of the beryllium substrate coupon was then coated with silver by a hot hollow cathode coating process, thereby depositing a layer of silver 34 on top of the chromium layer 30 and a similar layer of silver 36 applied to the opposite end surface 32 of the substrate coupon.

The hot hollow cathode process was also used to apply a layer of silver 38 to the end of an elongated copper pulling rod 40 as shown in detail in FIG. 4. A similar pulling rod 42 was prepared having a similar silver coating 44 secured to one end thereof as shown in FIG. 5. The copper bars or pulling rods 40 and 42 were then attached to opposite surfaces of the coupon 14 as shown in FIG. 5 of the drawings in order to effect a silver-to-silver bond of the layers 34 and 44 and a silver-to-silver bond of the layers 36 and 38. These parts were joined by a solid state bonding technique wherein the material was raised to 200 degrees centigrade and an axial compressive load of 20,000 pounds per square inch was applied for 10 minutes.

After bonding, the assembly was machined into the tensile test specimen shown in FIG. 5 whereby the region containing the specimen 14 is of uniform diameter, thereby leaving a pair of enlarged portions 46 and 48 at the ends of the assembly for ease of handling in a tensile test fixture.

The gauge length of the test assembly described herein was much more slender than the 4:1 length-to-diameter ratio specified by ASTM practice. This was because the coated regions are very thin and therefore have a very limited amount of absolute ductility. Thus, in a tensile test the bond behaves in a manner similar to a brittle material and is therefore sensitive to moment (rotational) type loading caused by misalignment in the test fixture. These loading moments can cause premature failure of the joint. The copper, by virtue of its comparatively low modulus combined with the slenderness of the rod, helps distribute misalignment displacements and stress, to a great extent avoiding an uneven stress build-up in the coating and bond region.

Data for the adhesion test described herein on one set of specimens tested are shown in the Table herein. All but one specimen failed entirely along the chromium-beryllium interface, and that failure could probably have been avoided had the copper bars been lapped. Standard deviations are considered to be small for this type of test, and the data clearly indicates a slightly greater adhesion at the pole position of the hemispherical shell.

TABLE

| Sample No. | Sample Location | Stress at Failure | % Be—Cr Failure | Ave* (ksi) | Standard Deviation (ksi) |
|---|---|---|---|---|---|
| W-33 | waist | 8.28 | 90 | | |
| W-35 | waist | 7.60 | 100 | | |
| W-36 | waist | 7.61 | 100 | 7.01 | 1.01 |
| W-37 | waist | 5.75 | 100 | | |
| W-39 | waist | 5.80 | 100 | | |
| W-40 | waist | 7.35 | 100 | | |
| P-34 | pole | 9.69 | 100 | | |
| P-35 | pole | 7.93 | 100 | 8.70 | .73 |
| P-36 | pole | 8.67 | 100 | | |
| P-38 | pole | 8.50 | 100 | | |

*P-39 was not included among the samples averaged because the failure did not occur entirely at the Be—Cr interface.

From the foregoing it is apparent that the present invention teaches a method for conducting precise quantitative measurements of metal coating adhesion on a substrate material. Whereas the present invention has been particularly described in connection with the example depicted in the drawings, it is apparent that the method may be utilized for obtaining quantitative adhesion strength measurements of a variety of coatings upon a variety of substrate materials.

I claim:

1. A method for measuring metal coating adhesion to a substrate material comprising the steps of:
    (a) preparing a test coupon of substrate material having the metal coating applied to one surface thereof by a first coating process;
    (b) coating said one surface of the coupon and the opposite surface thereof with a second metal by way of a second coating process to provide an adhesion strength greater than that of the coating adhesion to be measured;
    (c) coating one end of each of two pulling rods with said second metal by way of said second coating process;
    (d) joining the coated end of one pulling rod with the coated end of said one surface of the coupon and the coated end of the other pulling with the coated opposite surface of the coupon by a solid state bonding process; and
    (e) applying instrumented static tensile loading to the pulling rods until fracture of the metal coating adhesion to the substrate material occurs.

2. A method as set forth in claim 1 wherein the first coating process is a physical vapor deposition process.

3. A method as set forth in claim 1 wherein the second coating process is a hot hollow cathode process.

4. A method as set forth in claim 1 wherein the second metal is silver.

5. The method as set forth in claim 1 wherein the second metal is gold.

6. The method as set forth in claim 1 and including the step of machine turning the test coupon and attached pulling rods to a uniform diameter in a region containing the coupon prior to application of tensile loading.

7. The method as set forth in claim 1 wherein the solid state bonding process comprises moderate temperature, high compression loading for a given time duration.

8. A method as set forth in claim 1 wherein the substrate material is beryllium and the metal coating is chromium, the first coating process being physical vapor deposition, said second metal being silver, said second coating process being hot hollow cathode.

* * * * *